United States Patent [19]

Nesvadba

[11] Patent Number: 5,428,177
[45] Date of Patent: Jun. 27, 1995

[54] 3-(DIHYDROBENZOFURAN-5-YL)BEN-ZOFURAN-2-ONES AS STABILIZERS

[75] Inventor: Peter Nesvadba, Marly, Switzerland

[73] Assignee: Ciba-Geigy Corporation, Ardsley, N.Y.

[21] Appl. No.: 124,138

[22] Filed: Sep. 20, 1993

[30] Foreign Application Priority Data

Sep. 23, 1992 [CH] Switzerland .................. 2980/92

[51] Int. Cl.⁶ ............................................ C07D 307/28
[52] U.S. Cl. .................................. 549/304; 549/305; 549/307; 524/109
[58] Field of Search ................... 549/304, 305, 307

[56] References Cited

U.S. PATENT DOCUMENTS

| 3,862,133 | 1/1975 | Layer | 260/343.3 |
| 4,325,863 | 4/1982 | Hinsken et al. | 624/111 |
| 4,338,244 | 7/1982 | Hinsken et al. | 524/109 |
| 4,366,240 | 12/1982 | Lässig et al. | 430/542 |
| 5,175,312 | 12/1992 | Dubs et al. | 549/307 |

FOREIGN PATENT DOCUMENTS

| 0146269 | 6/1985 | European Pat. Off. |
| 0415887 | 3/1991 | European Pat. Off. |
| 0182507 | 12/1991 | European Pat. Off. |
| 3006268 | 8/1981 | Germany |
| 2944295 | 5/1982 | Germany |
| 4202276 | 8/1992 | Germany |
| 647773 | 2/1985 | Switzerland |
| 2034308 | 6/1990 | United Kingdom |
| 2257141 | 1/1993 | United Kingdom |
| 8001566 | 8/1980 | WIPO |

OTHER PUBLICATIONS

C. S. Foote et al., J. Amer. Chem. Soc. 95, 586–588 (1973).
Houben-Weyl, Methoden der Organischen Chemie, vol. 6/1C, 1030 1976.
W. Bradley et al, J. Chem. Soc. (1956), 1622–1627.
M. Auger et al., Bull. Soc. Chim. FR, (1970) 4024–4030.
L. Jurd, Aust. J. Chem. 31, 347–352 (1978).

*Primary Examiner*—C. Warren Ivy
*Assistant Examiner*—A. A. Owens
*Attorney, Agent, or Firm*—Luther A. R. Hall

[57] ABSTRACT

Novel compounds of formula (1)

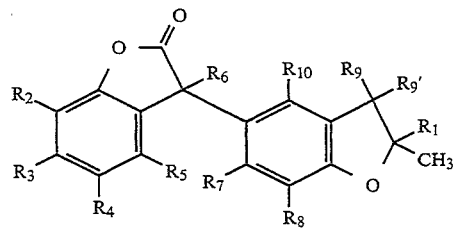

wherein $R_1$ is hydrogen, alkyl or alkaryl, $R_2$ to $R_5$ are independently hydrogen, chloro, alkyl phenylalkyl, aryl, cycloalkyl, alkoxy, alkylthio, hydroxy, amino or substituted amino, $R_6$ is hydrogen, $R_7$ and $R_8$ are hydrogen or alkyl, $R_9$ and $R_9'$ are hydrogen, alkyl or phenyl, and $R_{10}$ is hydrogen or alkyl, are disclosed as stabilisers for protecting organic materials against thermal, oxidative or light-induced degradation.

6 Claims, No Drawings

3-(DIHYDROBENZOFURAN-5-YL)BENZOFURAN-2-ONES AS STABILIZERS

The present invention relates to novel 3-(dihydrobenzofuran-5-yl)benzofuran-2-ones, to compositions comprising an organic material, preferably a polymer, and the novel stabilisers, and to the use thereof for stabilising organic materials against oxidative, thermal or light-induced degradation.

Individual 3-(alkoxyphenyl)benzofuran-2-ones have been described, inter alia, by M. Auger et al, Bull. Soc. Chim. Fr. 1970, 4024; L. Jurd, Aust. J. Chem., 31,347 (1978) and C. S. Foote et at, J. Amer. Chem. Soc. 95, 586 (1973), and in DE-A-3 006 268.

The use of some benzofuran-2-ones as stabilisers for organic polymers is disclosed, inter alia, in U.S. Pat. No. 4,325,863; U.S. Pat. No. 4,338,244 and EP-A-415,887.

It has now been found that a selected group of such benzofuran-2-ones are especially suitable for use as stabilisers for organic materials which are susceptible to oxidative, thermal or light-induced degradation.

Specifically, the invention relates to compounds of formula (1)

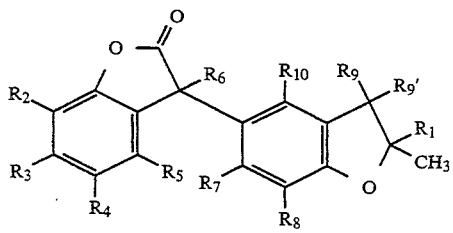

wherein $R_1$ is hydrogen, $C_1$-$C_4$alkyl, unsubstituted or $C_1$-$C_4$alkyl-substituted phenyl, $R_2$, $R_3$, $R_4$ and $R_5$ are each independently of the other hydrogen, chloro, $C_1$-$C_{25}$alkyl, $C_7$-$C_9$phenylalkyl, unsubstituted or $C_1$-$C_4$alkyl-substituted phenyl, unsubstituted or $C_1$-$C_4$alkyl-substituted $C_5$-$C_8$cycloalkyl; $C_1$-$C_{18}$alkoxy, $C_1$-$C_{18}$alkylthio, hydroxy, $C_1$-$C_4$alkylamino, di($C_1$-$C_4$alkyl)amino, $C_1$-$C_{25}$alkanoyloxy, $C_1$-$C_{25}$alkanoylamino, $C_3$-$C_{25}$alkenoyloxy, $C_3$-$C_{25}$alkanoyloxy which is interrupted by oxygen, sulfur or

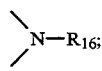

$C_6$-$C_9$cycloalkylcarbonyloxy, benzoyloxy, or $C_1$-$C_{12}$alkyl-substituted benzoyloxy, or $R_2$ and $R_3$ or $R_3$ and $R_4$ or $R_4$ and $R_5$, together with the linking carbon atoms, form a phenyl ring, $R_4$ is additionally —$(CH_2)_n$—$COR_{11}$, or, if $R_3$, $R_5$, $R_6$, $R_7$ and $R_{10}$ are hydrogen, $R_4$ is additionally a radical of formula (2)

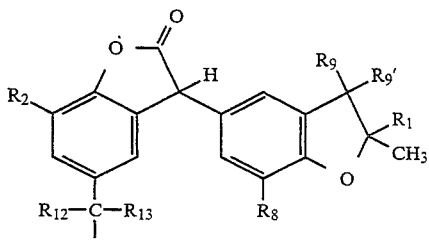

$R_6$ is hydrogen or a radical of formula (3)

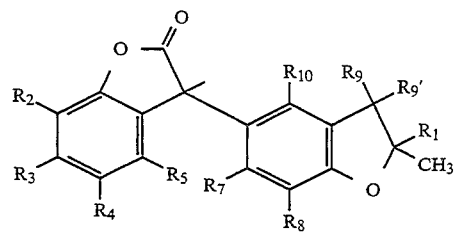

wherein $R_4$ is not a radical of formula (2), $R_7$ and $R_8$ are each independently of the other hydrogen or $C_1$-$C_4$alkyl, $R_9$ and $R'_9$ are hydrogen, $C_1$-$C_4$alkyl or phenyl, with the proviso that at least one of $R_9$ and $R'_9$ is hydrogen, $R_{10}$ is hydrogen or $C_1$-$C_4$alkyl, $R_{11}$ is hydroxy,

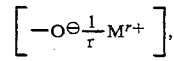

$C_1$-$C_{18}$alkoxy or

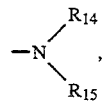

$R_{12}$ and $R_{13}$ are each independently of the other hydrogen, $CF_3$, $C_1$-$C_{12}$alkyl or phenyl, or $R_{12}$ and $R_{13}$, together with the linking carbon atom, form a $C_5$-$C_8$cycloalkylidene ring which is unsubstituted or substituted by 1 to 3 $C_1$-$C_4$alkyl groups; $R_{14}$ and $R_{15}$ are each independently of the other hydrogen or $C_1$-$C_{18}$alkyl, $R_{16}$ is hydrogen or $C_1$-$C_8$alkyl, M is a metal cation of valency r, n is 0, 1 or 2, and r is 1, 2 or 3.

Alkyl of up to 25 carbon atoms is a branched or unbranched radical and is typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. A preferred meaning of $R_2$ and $R_4$ is typically $C_1$-$C_8$alkyl. A particularly preferred meaning of $R_4$ is $C_1$-$C_4$alkyl.

$C_7$-$C_9$Phenylalkyl may typically be benzyl, α-methylbenzyl, α,α-dimethylbenzyl or 2-phenylethyl. Benzyl is preferred.

$C_1$-$C_4$Alkyl-substituted phenyl that preferably contains 1 to 3, preferably 1 or 2, alkyl groups, will typically be o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Unsubstituted or $C_1$-$C_4$alkyl-substituted $C_5$-$C_8$cycloalkyl is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl and tertbutylcyclohexyl are preferred.

Alkoxy of up to 18 carbon atoms is a branched or unbranched radical and is typically methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy.

Alkylthio of up to 18 carbon atoms is a branched or unbranched radical and is typically methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

Alkylamino of up to 4 carbon atoms is a branched or unbranched radical and is typically methylamino, ethylamino, propylamino, isopropylamino, n-butylamino, isobutylamino or tert-butylamino.

Di($C_1$-$C_4$)alkylamino also means that the two moieties, each independently of the other, are branched or unbranched, and is typically dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or diisobutylamino.

Alkanoyloxy of up to 25 carbon atoms is an unbranched or branched radical and is typically formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy.

Alkanoylamino of up to 25 carbon atoms is an unbranched or branched radical and is typically formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino or docosanoylamino.

Alkenoyloxy of 3 to 25 carbon atoms is an unbranched or branched radical and is typically propenoyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, isododecenoyloxy, oleoyloxy, n-2-octadecenoyloxy or n-4-octadecenoyloxy.

$C_3$-$C_{25}$Alkanoyloxy which is interrupted by oxygen, sulfur or

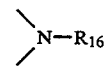

is typically $CH_3$—O—$CH_2$COO—, $CH_3$—S—$CH_2$COO—, $CH_3$—NH-$CH_2$COO—, $CH_3$—N($CH_3$)—$CH_2$COO—, $CH_3$—O—$CH_2CH_2$—O—$CH_2$COO—, $CH_3$—(O—$CH_2CH_2$—)$_2$O—$CH_2$COO—, $CH_3$—(O—$CH_2CH_2$—)$_3$O—$CH_2$COO— or $CH_3$—(O—$CH_2CH_2$—)$_4$O—$CH_2$COO—.

$C_6$-$C_9$Cycloalkylcarbonyloxy is typically cyclopentylcarbonyloxy, cyclohexylcarbonyloxy, cycloheptylcarbonyloxy or cyclooctylcarbonyloxy. Cyclohexylcarbonyloxy is preferred.

$C_1$-$C_{12}$Alkyl-substituted benzoyloxy is typically o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy.

A $C_1$-$C_4$alkyl-substituted $C_5$-$C_8$cycloalkylidene ring that preferably contains 1 to 3, most preferably 1 or 2, branched or unbranched alkyl groups, is typically cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Cyclohexylidene and tert-butylcyclohexylidene are preferred.

A mono-, di- or trivalent metal cation is preferably an alkali metal cation, an alkaline earth metal cation or an aluminium cation, typically $Na^+$, $K^+$, $Mg^{++}$, $Ca^{++}$ or $Al^{+++}$.

Preferred compounds of formula (1) are those wherein $R_1$ is hydrogen, $C_1$-$C_4$alkyl or phenyl, $R_2$, $R_3$, $R_4$ and $R_5$ are each independently of the other hydrogen, chloro, $C_1$-$C_{18}$alkyl, benzyl, phenyl, $C_5$-$C_8$cycloalkyl, $C_1$-$C_{18}$alkoxy, $C_1$-$C_{18}$alkylthio, $C_1$-$C_{18}$alkanoyloxy, $C_1$-$C_{18}$alkanoylamino, $C_3$-$C_{18}$alkenoyloxy or benzoyloxy, or $R_2$ and $R_3$ or $R_4$ and $R_5$, together with the linking carbon atoms, form a phenyl ring, or, if $R_3$, $R_5$, $R_6$, $R_7$ and $R_{10}$ are hydrogen, $R_4$ is additionally a radical of formula (2), $R_9$ and $R'_9$ are hydrogen or $C_1$-$C_4$alkyl, with the proviso that at least one of $R_9$ and $R'_9$ is hydrogen, and $R_{12}$ and $R_{13}$ are either methyl groups or, together with the linking carbon atom, form a $C_5$-$C_8$cycloalkylidene ring which is unsubstituted or substituted by 1 to 3 $C_1$-$C_4$alkyl groups.

Further preferred compounds of formula (1) are those wherein at least two of $R_2$, $R_3$, $R_4$ and $R_5$ are hydrogen.

Also preferred are compounds of formula (1), wherein $R_3$ and $R_5$ are hydrogen. Particularly preferred give compounds of formula (1) are those wherein $R_1$ is hydrogen or $C_1$-$C_4$alkyl, $R_2$ and $R_4$ are each independently of the other hydrogen, $C_1$-$C_{18}$alkyl, benzyl, phenyl, $C_5$-$C_8$cycloalkyl or $C_1$-$C_{18}$alkoxy, or, if $R_3$, $R_5$, $R_6$, $R_7$ and $R_{10}$ are hydrogen, $R_4$ is additionally a radical of formula (2), $R_3$ and $R_5$ are each independently of the other hydrogen or $C_1$-$C_4$alkyl, $R_6$ is hydrogen or a radical of formula (3), wherein $R_4$ is not a radical of formula (2), $R_7$, $R_8$, $R_9$, $R'_9$ and $R_{10}$ are hydrogen, and $R_{12}$ and $R_{13}$ are either methyl groups or, together with the linking carbon atom, form a $C_5$-$C_8$cycloalkylidene ring.

Of very particular interest are compounds of formula (1), wherein $R_1$ is hydrogen or methyl, $R_2$ is hydrogen or $C_1$-$C_{18}$alkyl, $R_3$, $R_5$, $R_7$, $R_8$, $R_9$, $R'_9$ and $R_{10}$ are hydrogen, $R_4$ is hydrogen or $C_1$-$C_4$alkyl, or, if $R_6$ is hydrogen, $R_4$ is additionally a radical of formula (2), $R_6$ is hydrogen or a radical of formula (3), wherein $R_4$ is not a radical of formula (2), and $R_{12}$ and $R_{13}$ are either methyl groups or, together with the linking carbon atom, form a cyclohexylidene ring.

The novel compounds of formula (1) can be prepared in per se known manner.

A convenient and preferred process for the preparation of the compounds of formula (1) comprises reacting a phenol of formula (4)

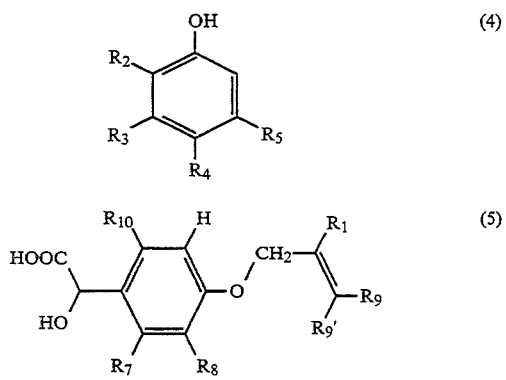

wherein $R_2$, $R_3$, $R_4$ and $R_5$ have the given meanings, with an allyloxymandelic acid derivative of formula (5) in which the phenyl ring is substituted and wherein $R_1$, $R_7$, $R_8$, $R_9$, $R'_9$ and $R_{10}$ have the given meanings, at elevated temperature, preferably in the range from 130° to 200° C., in the melt or in a solvent under normal or slightly reduced pressure to compounds of formula (6)

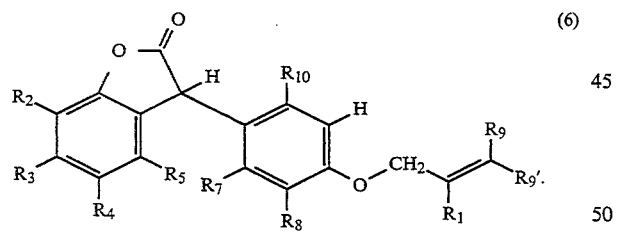

The reaction is preferably carried out in a solvent, conveniently acetic acid or formic acid, in the temperaturerange from 50° to 130° C. The reaction can be catalysed by the addition of an acid such as hydrochloric acid, sulfuric acid or methanesulfonic acid. The reaction can be carried out as described in the references cited in the introduction to the description.

The mandelic acids of formula (5) in which the phenyl ring is substituted are known from the literature or can be prepared in general accordance with the method described by W. Bradley et al, J. Chem. Soc. 1956, 1622, or according to EP-A-146 269, EP-B-182 507 (Example 1, page 4) or DE-A-2 944 295.

The phenols of formula (4) are also known or can be prepared by methods which are known per se.

Bisphenols of formula (7)

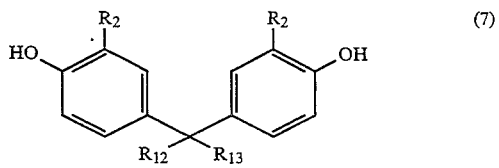

can be prepared in accordance with Houben-Weyl, Methoden der organischen Chemie, Vol. 6/1c, 1030.

The compounds of formula (6) are rearranged under the conditions of a Claisen rearrangement at elevated temperature, preferably in the temperature range from 200° to 240° C., in the melt or in a solvent, to the compounds of formula (8)

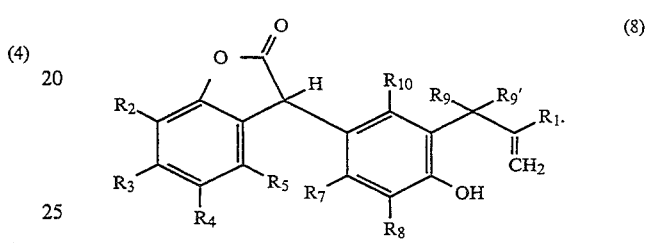

These compounds can be isolated or cyclised directly, without purification, in a solvent such as acetic acid with a catalytic amount of a strong acid, conveniently methanesulfonic acid, at elevated temperature, preferably in the temperature range from 50° to 130° C., to give the compounds of formula (1).

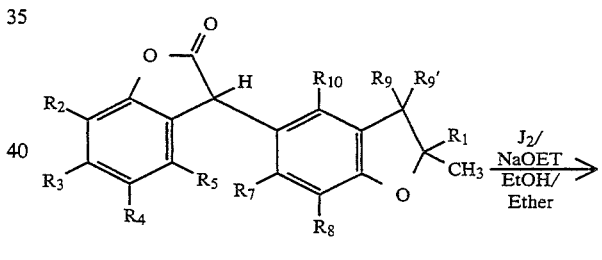

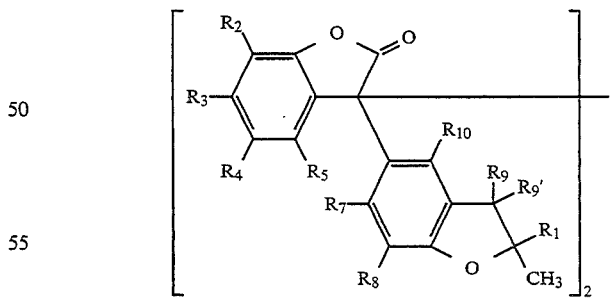

The dimerisation of compounds of formula (9) to prepare compounds of formula (1), wherein $R_6$ is a group of formula (3) [compounds of formula (10)] is carried out by oxidation, conveniently with iodine under basic conditions in an organic solvent at room temperature. A suitable base is preferably sodium ethylate and preferred suitable solvents are ethanol and diethyl ether.

The compounds of formula (1) are suitable for stabilising organic materials against thermal, oxidative or light-induced degradation.

Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopenlene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst stystems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

5. Polystyrene, poly(p-methylstyrene), poly(la-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrenelroutadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or NES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 ) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose buryrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Further objects of the invention are thus also compositions comprising an organic material which is subject to oxidative, thermal or light-induced degradation and at least one compound of formula (1).

Preferred organic materials are polymers, typically synthetic polymers, preferably thermoplastic polymers. Especially preferred organic materials are polyacetals or polyolefins such as polypropylene or polyethylene.

To be singled out for special mention is the efficacy of the novel compounds against thermal and oxidative degradation, especially under the action of heat which occurs during the processing of thermoplasts. The compounds of this invention are therefore admirably suited for use as processing stabilisers.

The compounds of formula (1) will preferably be added to the organic material to be stabilised in concentrations of 0.0005 to 5%, preferably 0.001 to 2%, typically 0.01 to 2%, based on the weight of said material.

In addition to comprising the compounds of formula (1), the inventive compositions may comprise further co-stabilisers, typically the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-( 3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydlmxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2]octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, penlmerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)-propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$] $_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-yl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4- piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopmpylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopmpyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadccyl phosphite, distearyl pentaerythritol diphosphite, tris(2,4-di-tert-butylphenyl)

phosphite, diisodccyl pentaerythritol diphosphite, bis(2,4-di-tert-butylphenyl) pentaerythritol diphosphite, bis(2,6-di-tert-butyl-4-methylphenyl)-pentaerythritol diphosphite, diisodccyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc: dibutyldithiocarbamate, dioctadecyl disulfide, pentaerythritol tetrakis(β-dodecylmelxcapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The co-stabilisers are typically used in concentrations of 0.0 1 to 10 %, based on the total weight of the material to be stabilised.

The novel compounds of formula (1), can be used in particular together with phenolic antioxidants. The novel compositions therefore preferably comprise, in addition to compounds of formula (1), phenolic: antioxidants, preferably those listed in 1.1 to 1.16 of the foregoing list of co-stabilisers.

Other preferred compositions comprise, in addition to the compounds of formula (1), at least one organic phosphite or phosphonite.

The compounds of formula (1) and other optional additives are incorporated into the organic polymer by known methods, conveniently before or during shaping to moulded articles or alternatively by coating the organic polymers with a solution or dispersion of the compounds and subsequently evaporating the solvent. The compounds of formula (1) can also be added to the materials to be stabilised in the form of a masterbatch which contains these compounds, typically in a concentration of 2.5 to 25% by weight.

The compounds of formula (1) can also be added before or during polymerisation or before crosslinking.

The compounds of formula (1) can be incorporated into the organic polymer in pure form or in waxes, oils or polymer encapsulations.

The compounds of formula (1) can also be sprayed on to the polymer to be stabilised. They are able to dilute other additives (typically the conventional additives listed above) or melts thereof, so that they can also be sprayed together with these additives on to the polymer to be stabilised. Application by spraying during deactivation of the polymerisation catalysts is especially advantageous, in which case spraying is conveniently effected with the vapour used for deactivation.

It may be expedient to spray the compounds of formula (1), with or without other additives, on to spherical polymerised polyolefins.

A preferred embodiment of this invention is therefore the use of compounds of formula (1) for stabilising an organic material against oxidative, thermal or light-induced degradation.

The stabilised materials may be in any form of presentation, typically sheets, filaments, ribbons, mouldings, profiles or binders for coating compositions, adhesives or putties.

The invention also relates to a process for stabilising an organic material against oxidative, thermal or light-induced degradation, which comprises incorporating therein or applying thereto at least one compound of formula (1).

As already emphasised, the novel compounds are used with particular advantage as stabilisers in polyolefins, preferably as heat stabilisers. Excellent stabilisation is achieved when the compounds are used in conjunction with organic phosphites or phosphonites. The novel compounds have in this case the advantage that they are effective in exceedingly low concentration, typically of 0.0001 to 0.015% by weight, preferably of 0.0001 to 0.008% by weight, based on the polyolefin. The organic phosphite or phosphonite is conveniently used in a concentration of 0.01 to 2% by weight, preferably of 0.01 to 1% by weight, based on the polyolefin. It is preferred to use the organic phosphites and phosphonites disclosed in DE-A-4 202 276. Attention is drawn in particular to the claims, to the Examples and to pages 5, last paragraph, to 8. Particularly suitable phosphites and phosphonites will also be found under item 4 of the above list of co-stabilisers.

The invention is illustrated in more detail by the following Examples in which parts and percentages are by weight.

EXAMPLE 1

Preparation of 5,7-di-tert-butyl-3-(2-methyl-dihydrobenzofuran-5-yl)benzofuran-2-one (Compound (101), Table 1).

3.80 g (10.0 mmol) of 3-(4-allyloxyphenyl)-5,7-di-tert-butyl-benzofuran-2-one are kept under nitrogen for about 4 hours at 220° C. After cooling, 10 ml of acetic acid and 0.3 ml of methanesulfonic acid are added and the reaction mixture is refluxed for 7 hours. After dilution with 100 ml of water, the product is extracted with dichloromethane. The organic phases are washed with water, combined, dried over sodium sulfate and concentrated on a vacuum rotary evaporator. Chromatography of the residue on silica gel with the eluant system dichloromethane/hexane=1:2 and crystallisation of the pure fractions from ligroin gives 1.07 g (28%)of 5,7-di-tert-butyl-3-(2-methyl-dihydrobenzofuran-5-yl)benzofuran-2-one, m.p. 136°–152° C. as a mixture of diastereoisomers (compound (101), Table 1).

The starting 3-(4-allyloxyphenyl)-5,7-di-tert-butyl-benzofuran-2-one can be prepared as follows:

A mixture of 309 g (1.50 mol) of 2,4-di-tert-butylphenol and 192 g (1.00 mol) of 4-allyloxymandelic acid (prepared in accordance with EP-B-182 507, Example 1, page 4) is stirred under nitrogen for 2 hours at 140°–150° C. Then the mixture is stirred under low vacuum (50 mbar) for 1.5 hours; at 150° C. Excess 2,4-di-tert-butylphenol is distilled off under a high vacuum. Crystallisation of the residue from xylene and ethanol gives 230.1 g (61%) of 3-(4-allyloxyphenyl)-5,7-di-tert-butylbenzofuran-2-one of m.p. 112°–114° C.

Preparation of 4-Allyoxymandelic Acids 20.8 g (0.10 mol) of 4-hydroxymandelic acid sodium salt monohydrate and 6.6 g (0.10 mol) of potassium hydroxide are dissolved with 1.0 g (6.7 mmol) of sodium iodide in 75 ml of methanol. Then 0.12 mol of allyl bromide (methallyl chloride in the case of methallyl) is added and the reaction mixture is refluxed for 16 hours under nitrogen. The reaction mixture is concentrated on a vacuum rotary evaporator and the residue is acidified with concentrated hydrochloric acid. The product is extracted 3 times with butyl acetate. The organic phases are washed with water, combined, dried over sodium sulfate and concentrated on a vacuum rotary evaporator. Crystallisation of the residue from toluene/petroleum ether give 4-allyloxymandelic acids such as 4-allyloxymandelic acid as an amorphous powder (70%) and 4-methallyloxymandelic acid, m.p. 121°–126° (65%).

Preparation of Substituted 4-Hydroxymandelic Acids 0.30 mol of starting phenol (e.g. o-cresol, 2-tert-butylphenol or 2-isopropyl-3-methylphenol) is dissolved in 150 ml of 2N sodium hydroxide solution under nitrogen. After cooling to +5° C., 4.8 g (0.12 mol) of sodium hydroxide and 13.3 ml (0.12 mol) of 50% aqueous glyoxylic acid are added and the reaction mixture is stirred for 4 hours at room temperature. A further 0.12 mol of sodium hydroxide and glyoxylic acid is each added twice (total 0.36 mol) at 4 hour intervals. The reaction mixture is then stirred for 12 hours, then neutralised with concentrated hydrochloric acid and washed with 2×75 ml of petroleum ether. The aqueous phase is then acidified with concentrated hydrochloric acid and repeatedly extracted with ether. The organic phases are combined, dried over magnesium sulfate and concentrated on a vacuum rotary evaporator to give the following compounds: 4-hydroxy-3-methylmandelic acid, m.p. 115°–120° C., yield 55%; 4-hydroxy-3-tert-butylmandelic acid, m.p. 156°–158° C., Yield 26%; and 3-isopropyl-4-hydroxy-2-methylmandelic acid, m.p. 114°–119° C., Yield 20%.

EXAMPLE 2

Preparation of 3-(2,2-Dimethyldihydrobenzofuran-5-yl)-5,7-di-tert-butylbenzofuran-2-one (Compound (102), Table 1)

A mixture of 20.6 g (0.10 mol) of 2,4-di-tert-butylphenol and 22.6 g (0.10 mol) of 4-methallyloxymandelic acid (preparation as in Example 1) is kept at 155° C. under reduced pressure (50 mbar) for 8 hours. The reaction mixture is then heated to 220° C. under nitrogen and kept at this temperature for about 100 minutes. After cooling to about 120° C., 100 ml of acetic acid and 2 ml of methanesulfonic acid are added and the solution is refluxed for 3 hours. The reaction mixture is cooled, and the product is precipitated with 10 ml of ethanol and isolated by filtration. Recrystallisation from ethanol (100 ml)/acetic acid (8 ml) gives 8.0 g (20%) of 3-(2,2-dimethyldihydrobenzofuran-5-yl)-5,7-di-tert-butylbenzofuran-2-one, m.p. 164°–166° C. (compound (102), Table 1).

In accordance with the general procedure of Example 2, the compounds (103) and (104) are prepared from the corresponding phenols and 4-methallyloxymandelic acid. In the preparation of compound (104), 2 equivalents of 4omethallyloxymandelic acid are used with respect to the bisphenol employed.

EXAMPLE 3

Preparation of 3,3'-Bis[3-(2,2-dimethyldihydrobenzofuran-5-yl)-5,7-di-tert-butylbenzofuran-2-one] (Compound (105), Table 1)

11.77 g (30 mmol) of 3-(2,2-dimethyldihydrobenzofuran-5-yl)-5,7-di-tert-butylbenzofuran-2-one (compound (102), Example 2) are added, under nitrogen, to a solution of sodium methylate (prepared by addition of 0.69 g (30.0 mmol) of sodium to 120 ml of absolute methanol). Then a solution of 3.8 g (15.0 mmol) of iodine in 60 ml of diethyl ether is added dropwise at room temperature over about 10 minutes. The reaction mixture is stirred for 30 minutes, thereafter diluted with 500 ml of water and extracted with 3×100 ml of diethyl ether. The organic phases are separated, washed with water, combined, dried over magnesium sulfate and concentrated on a vacuum rotary evaporator. Two crystallisations of the residue from methanol give 3.1 g (26%) of 3,3'-bis[3-(2,2-dimethyldihydrobenzofuran-5-yl)-5,7-di-tert-butylbenzofuran-2-one], m.p. 202°–210° C. (compound (105), Table 1).

TABLE 1

| No. | Compound | m.p. (°C.) | C(%), H(%) (calcd/found) | Yield (%) |
|---|---|---|---|---|
| 101 | 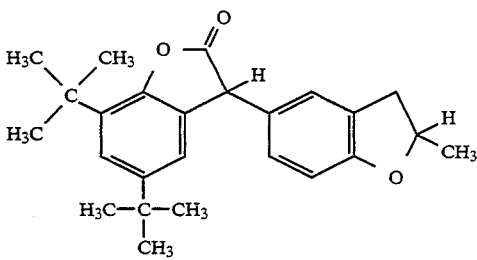 | 136–152 | 79.33 7.99<br>79.34 7.99<br>Mixture of diastereoisomers | 28 |

TABLE 1-continued

| No. | Compound | m.p. (°C.) | C(%), H(%) (calcd/found) | Yield (%) |
|---|---|---|---|---|
| 102 | | 164–166 | 79.56 8.22<br>79.33 8.35 | 20 |
| 103 | | 69–86 | 81.27 9.95<br>81.27 9.93<br>mixture of diastereoisomers | 50 |
| 104 | | resin | characterised by MS for C₅₀H₅₆O₆<br>calcd M⁺ = 752.99<br>found M⁺ = 753.0<br>mixture of diastereoisomers | 75 |
| 105 | | 202–210 | 79.97 7.74<br>79.53 7.96 | 26 |

EXAMPLE 4

Stabilisation of Multiple-Extruded Polypropylene 1.3 kg of polypropylene powder (Profax 6501), which has been prestabilised with 0.025% of Irganox ® 1076 (n-octadecyl 3-[3,5-di-tert-butyl-4-hydroxyphenyl]propionate (melt index 3.2, measured at 230° C./2.16 kg) are blended with 0.05% of Irganox ® 1010 (pentaerythritol tetrakis[3-(3,5-di-tert-butyl-4-hydroxyphenyl)propionate), 0.05% of calcium stearate, 0.03% of DHT 4A ® (Kyowa Chemical Industry Co., Ltd., [Mg$_{4.5}$Al$_2$-(OH)$_{13}$CO$_3$·3,5H$_2$O]) and 0.015% of compound of Table 1. This blend is then extruded in an extruder having a cylinder diameter of 20 mm and a length of 400 mm at 100 rpm, the 3 heating zones being adjusted to the following temperatures: 260°, 270°, 280° C. The extrudate is cooled by drawing it through a water bath and is then granulated. This granulate is repeatedly extruded. After 3 extrusions, the melt index is measured (at 230° C./2.16 kg). A substantial increase in the melt index denotes pronounced chain degradation, i.e. poor stabilisation. The results are shown in Table 2.

TABLE 2

| Compound of Table 1 | Melt index after 3 extrusions |
|---|---|
| — | 20.0 |
| 101 | 5.3 |
| 102 | 5.9 |
| 103 | 5.6 |

EXAMPLE 5

Stabilisation of Polyethylene During Processing 100 parts of polyethylene powder (Lupolen ® 5260 Z) are blended with 0.05 part of pentaerythritol tetrakis[3-(3,5-di-tert-butyl-4-hydroxyphenyl)propionate], 0.05 parts of tris(2,4-di-tert-butylphenyl)phosphite and 0.05 part of compound of Table 1 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 3 as a measure of the stabilising action. The longer this time is the better the stabilising action.

TABLE 3

| Compound of Table 1 | Time until increase in torque (min) |
|---|---|
| — | 9.0 |
| 101 | 34.5 |
| 102 | 28.5 |
| 103 | 32.5 |

What is claimed is:
1. A compound of formula (1)

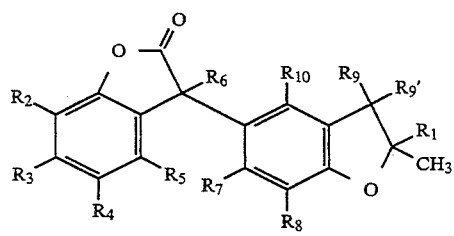

wherein $R_1$ is hydrogen, $C_1$-$C_4$alkyl, unsubstitued or $C_1$-$C_4$alkyl-substituted phenyl, $R_2$, $R_3$, $R_4$ and $R_5$ are each independently of the other hydrogen, chloro, $C_1$-$C_{25}$alkyl, $C_7$-$C_9$phenylalkyl, unsubstituted or $C_1$-$C_4$alkyl-substituted phenyl, unsubstituted or $C_1$-$C_4$alkyl-substituted $C_5$-$C_8$cycloalkyl; $C_1$-$C_{18}$alkoxy, $C_1$-$C_{18}$alkylthio, hydroxy, $C_1$-$C_4$alkylamino, di($C_1$-$C_4$alkyl)amino, $C_1$-$C_{25}$alkanoyloxy, $C_1$-$C_{25}$alkanoylamino, $C_3$-$C_{25}$alkenoyloxy, $C_3$-$C_{25}$alkanoyloxy which is interrupted by oxygen, sulfur or

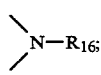

$C_6$-$C_9$cycloalkylcarbonyloxy, benzoyloxy or $C_1$-$C_{12}$alkyl-substituted benzoyloxy, or $R_2$ and $R_3$ or $R_3$ and $R_4$ or $R_4$ and $R_5$, together with the linking carbon atoms, form a phenyl ring, $R_4$ is additionally —(CH$_2$)$_n$—COR$_{11}$, or when $R_3$, $R_5$, $R_6$, $R_7$ and $R_{10}$ are hydrogen, $R_4$ is additionally a radical of formula (2)

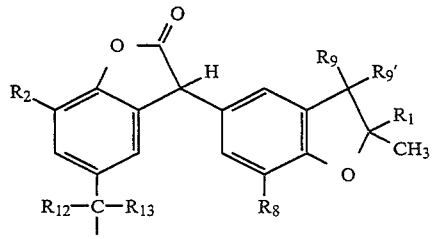

$R_6$ is hydrogen or a radical of formula (3)

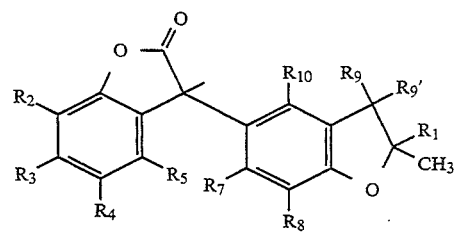

wherein $R_4$ is not a radical of formula (2), $R_7$ and $R_8$ are each independently of the other hydrogen or $C_1$-$C_4$alkyl, $R_9$ and $R'_9$ are hydrogen, $C_1$-$C_4$alkyl or phenyl, with the proviso that at least one of $R_9$ and $R'_9$ is hydrogen, $R_{10}$ is hydrogen or $C_1$-$C_4$alkyl, $R_{11}$ is hydroxy,

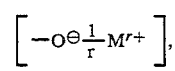

$C_1$-$C_{18}$alkoxy or

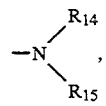

$R_{12}$ and $R_{13}$ are each independently of the other hydrogen, CF$_3$, $C_1$-$C_{12}$alkyl or phenyl, or $R_{12}$ and $R_{13}$, together with the linking carbon atom, form a $C_5$-$C_8$cycloalkylidene ring which is unsubstituted or substituted by 1 to 3 $C_1$-$C_4$alkyl groups; $R_{14}$ and $R_{15}$ are each independently of the other hydrogen or $C_1$-$C_{18}$alkyl, $R_{16}$ is hydrogen or $C_1$-$C_8$alkyl, M is a metal cation of valency r, n is 0, 1 or 2, and r is 1, 2 or 3.

2. A compound according to claim 1, wherein $R_1$ is hydrogen, $C_1$-$C_4$alkyl or phenyl, $R_2$, $R_3$, $R_4$ and $R_5$ are each independently of the other hydrogen, chloro, $C_1$-$C_8$alkyl, benzyl, phenyl, $C_5$-$C_8$cycloalkyl, $C_1$-$C_{18}$alkoxy, $C_1$-$C_{18}$alkylthio, $C_1$-$C_{18}$alkanoyloxy, $C_1$-$C_{18}$alkanoylamino, $C_3$-$C_{18}$alkenoyloxy or benzoyloxy, or $R_2$ and $R_3$ or $R_4$ and $R_5$, together with the linking carbon atoms, form a phenyl ring, or, when $R_3$, $R_5$, $R_6$, $R_7$ and $R_{10}$ are hydrogen, $R_4$ is additionally a radical of formula (2), $R_9$ and $R'_9$ are hydrogen or $C_1$-$C_4$alkyl, with the proviso that at least one of $R_9$ and $R'_9$ is hydrogen, and $R_{12}$ and $R_{13}$ are either methyl groups or, together with the linking carbon atom, form a $C_5$-$C_8$cycloalkylidene ring which is unsubstituted or substituted by 1 to 3 $C_1$-$C_4$alkyl groups.

3. A compound according to claim 1, wherein at least two of $R_2$, $R_3$, $R_4$ and $R_5$ are hydrogen.

4. A compound according to claim 1, wherein $R_3$ and $R_5$ are hydrogen.

5. A compound according to claim 1, wherein $R_1$ is hydrogen or $C_1$-$C_4$alkyl, $R_2$ and $R_4$ are each independently of the other hydrogen, $C_1$-$C_{18}$alkyl, benzyl, phenyl, $C_5$-$C_8$cycloalkyl or $C_1$-$C_{18}$alkoxy, or, when $R_3$, $R_5$, $R_6$, $R_7$ and $R_{10}$ are hydrogen, $R_4$ is additionally a radical of formula (2), $R_3$ and $R_5$ are each independently of the other hydrogen or $C_1$-$C_4$alkyl, $R_6$ is hydrogen or a radical of formula (3), wherein $R_4$ is not a radical of formula (2), $R_7$, $R_8$, $R_9$, $R'_9$ and $R_{10}$ are hydrogen, and $R_{12}$ and $R_{13}$ are either methyl groups or, together with the linking carbon atom, form a $C_5$-$C_8$cycloalkylidene ring.

6. A compound according to claim 1, wherein $R_1$ is hydrogen or methyl, $R_2$ is hydrogen or $C_1$-$C_{18}$alkyl, $R_3$, $R_5$, $R_7$, $R_8$, $R_9$, $R'_9$ and $R_{10}$ are hydrogen, $R_4$ is hydrogen or $C_1$-$C_4$alkyl, or, when $R_6$ is hydrogen, $R_4$ is additionally a radical of formula (2), $R_6$ is hydrogen or a radical of formula (3), wherein $R_4$ is not a radical of formula (2), and $R_{12}$ and $R_{13}$ are either methyl groups or, together with the linking carbon atom, form a cyclohexylidene ring.

* * * * *